United States Patent [19]

Rawson

[11] Patent Number: 4,518,396
[45] Date of Patent: May 21, 1985

[54] METHOD OF DEHYDRATING NATURAL GAS

[75] Inventor: William E. Rawson, Huntsville, Ala.

[73] Assignee: Gas Conditioning Industries, Inc., Huntsville, Ala.

[21] Appl. No.: 471,157

[22] Filed: Mar. 1, 1983

[51] Int. Cl.³ .............................................. C10K 1/16
[52] U.S. Cl. ................................... 48/196 R; 55/48; 568/621; 568/872
[58] Field of Search ................... 48/196 R; 55/32, 48; 568/872, 870, 621

[56] References Cited

U.S. PATENT DOCUMENTS

| | | |
|---|---|---|
| 2,381,055 | 9/1945 | Hoyt . |
| 2,615,812 | 10/1952 | Kaufman et al. ................... 568/872 |
| 2,615,924 | 10/1952 | Reents . |
| 2,684,331 | 7/1954 | Barman ............................... 568/872 |
| 2,771,193 | 11/1956 | Simpson et al. . |
| 2,772,206 | 11/1956 | Frankel et al. . |
| 2,772,237 | 11/1956 | Bauman et al. . |
| 3,040,104 | 6/1962 | Sarappo et al. ..................... 568/872 |
| 3,252,897 | 5/1966 | Hesler et al. . |
| 3,322,411 | 5/1967 | Moore ..................................... 55/32 |
| 3,563,954 | 2/1971 | Birmingham, Jr. . |
| 3,732,320 | 5/1973 | Ford ................................... 568/872 |
| 4,182,659 | 1/1980 | Anwer et al. ........................... 55/32 |
| 4,314,891 | 2/1982 | Knobel ................................... 55/32 |

FOREIGN PATENT DOCUMENTS

| | | | |
|---|---|---|---|
| 646805 | 8/1962 | Canada ................................. 568/872 |
| 595407 | 12/1947 | United Kingdom ................ 568/872 |

OTHER PUBLICATIONS

Stromquist et al., Glycerol by Ion Exchange, P&EC, pp. 1065–1070, vol. 43, May, 1951.

Primary Examiner—Peter Kratz
Attorney, Agent, or Firm—Cushman, Darby & Cushman

[57] ABSTRACT

Disclosed is a method and associated apparatus by which glycols may be cleaned, particularly those which have been used to dehydrate natural gas. Glycol contaminated with water, hydrocarbons, salts such as sodium chloride, and other impurities is degassed and physically separated from immiscible liquid hydrocarbons prior to passing through a quantity of absorbent material to remove the bulk of any residual hydrocarbons and filter particulates. The glycol is then routed through strong acid cation and strong base anion exchange resins to remove salts. The net product of the deionization is water which may easily be removed in a reboiler, yielding a clean, reusable glycol. Glycol which is not contaminated by petroleum impurity may be cleaned by strong acid cation and strong base anion exchange means alone.

5 Claims, 1 Drawing Figure

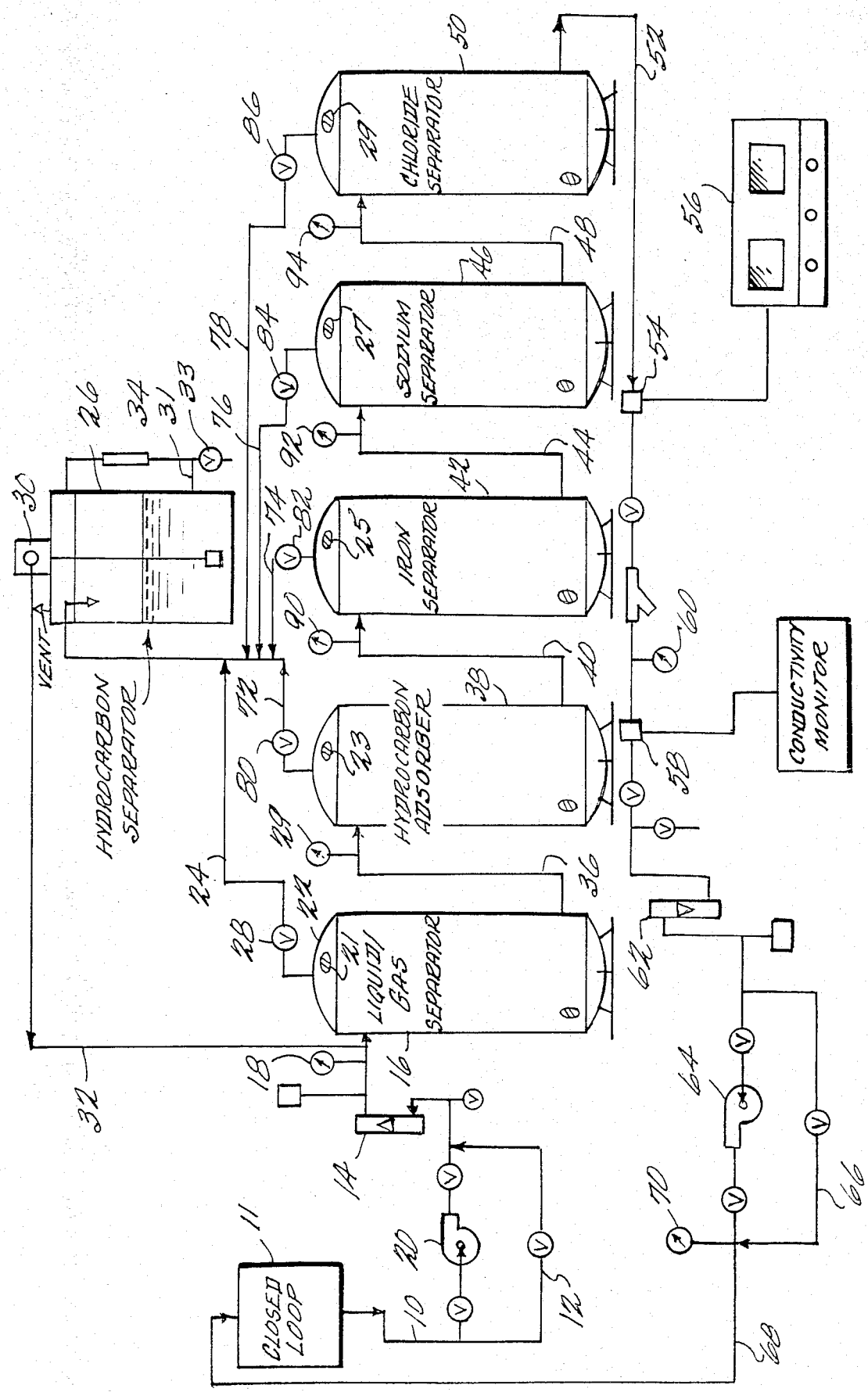

4,518,396

METHOD OF DEHYDRATING NATURAL GAS

FIELD OF THE INVENTION

This invention relates to a process and apparatus for cleaning and desalting glycols and, more particularly, to the use of ion exchange resins to perform the cleaning.

BACKGROUND OF THE INVENTION

Natural gas consists of a mixture of lower gaseous hydrocarbons occurring in the earth's crust. It frequently exists near crude oil deposits and is invariably mixed with, dissolved in, or otherwise associated with sizeable amounts of petroleum impurities. Other impurities, particularly water and various salts, are also frequently present in significant proportions. Thus freshly extracted natural gas presents formidable cleanup problems before it can ultimately be placed in a condition suitable for use by the consumer.

Natural gas is processed in conventional gas refining plants before being piped over long distances to various distribution points or use locations. For example, a main transporting pipeline may carry natural gas toward a city or other municipality until reaching a point wherein gas is tapped off through a reducing valve to travel through a secondary pipeline to its ultimate destination, storage facility, etc.

It is desirable that no water vapor be admitted to the transporting pipeline. Quantities of water or moisture that are relatively small compared to the quantities initially present when the gas is extracted from the earth may freeze and block the pipeline such that flow is completely halted or at least greatly restricted.

Additionally, freshly extracted natural gas may contain sizeable amounts of salts which are mostly in the form of sodium chloride and iron sulphide, but which are also present as other species. The corrosive action of salts on pipes and other facilities is well known to the gas-refining industry. Thus, the removal of water and salts from natural gas is commonly an integral function of any gas processing plant.

The means used nearly universally to accomplish the removal is a large tank equipped with baffles called an absorber. Natural gas arriving from many wells is admitted into the bottom of the absorber and upflows toward the top. At the same time a glycol, such as diethylene or triethylene glycol, is admitted continuously into the top of the tank and trickles downwardly over the baffles in countercurrent exchange with the upflowing gas. The net result is that the water and salts in the gas are exposed to and preferentially partition into the more polar glycol such that the gas exiting at the top of the absorber is substantially free of these contaminants.

Left behind, however, is a quantity of glycol typically running into the thousands of gallons which may be fouled with sizeable quantities of water, salts such as sodium chloride and iron sulphide, and oil or other crude petroleum contaminants. Water and salt-laden glycol is conventionally pumped through a closed-loop (of which the absorber is part) including various filters, strippers, heat exchangers, etc. and a reboiler wherein the glycol is conventionally heated and maintained at a temperature of from about 250° to about 400° F. such that the water quickly distills off. The glycol may then be returned through the remaining portion of the loop back to the absorber, again to flow in countercurrent exchange with contaminated natural gas.

A very troublesome problem arises herein, however, in that, although the reboiler can easily drive off water from the glycol, the salts and much of the crude oil contaminants remain therein. At times it may take but several trips through the loop before the glycol reaches its saturation point with respect to the salt. Salt starts to crystallize out and settle onto the heating pipes in the reboiler and forms a heat-insulating layer therein, and starts generally to foul the transport piping associated therewith. Ultimately the reboiler becomes so encrusted or corroded that the entire gas processing operation must be shut down and the reboiler must be dismantled and cleaned or repaired. The economic implications of a shutdown are so obvious as not to require description, in addition to which thousands of gallons of glycol must be discarded at a replacement cost close to four dollars per gallon.

Moreover, freshly extracted natural gas is frequently preliminarily stored in so-called "salt domes", i.e. giant cavities which have been artifically eroded into salt deposits by means of water and steam to depths of thousands of feet and diameters on the order of miles. The gas stored in these giant sodium chloride containers picks up even more salt and accordingly exacerbates the down-time problems at gas processing plants when it is re-extracted and processed.

Additionally, problems stemming from the presence of salts in natural gas is especially prevalent in offshore deep sea gas drilling operations. Here, a pipeline would be sunk through a few hundred feet of sea water before drilling through the floor for distances typically on the order of twenty thousand feet. After a "strike" has been made, gas at natural pressures carries the sea water head with it or otherwise absorbs large amounts of water and salt, all of which must be removed in refining operations.

Thus, the presence of salt in natural gas creates technological problems to which no satisfactory solution has yet been discovered. Clearly, a method of cleaning glycols which circumvents such thorny problems would be enthusiastically embraced by the petroleum-natural gas industry. Such a method would employ an apparatus to clean glycols which would be capable of feasibly being performed on-site and which would not require that the entire processing operation be shut down. Such a method and apparatus is the subject of the present invention.

Techniques for cleaning salts from various fluids have been known. For example, ion exchange resins have been used in the prior art to clean dissolved salts from various liquids. U.S. Pat. No. 3,615,924 to Reents discloses a method of purifying a relatively dilute aqueous glycerine solution, which method includes passing the solution through both cation and anion exchange resins. U.S. Pat. Nos. 3,252,897 to Hesler et al and 2,772,237 to Bauman also disclose the use of ion exchange resins to remove ionic impurities from a variety of liquids, including glycols, and are similar in that both disclose using a cation exchange resin in conjunction with a sulfated anion exchange resin to remove a strong acid or salt thereof from a series of liquids.

However, none of these patents contains any suggestion that strong acid cation (in the hydrogen ion form) and strong base anion (in the hydroxide ion form) exchange resins may be used in conjunction to clean relatively concentrated glycols, i.e. those solutions containing at least 80% glycol by volume, associated with the cleaning of natural gas. Nor do any of these patents suggest that ion exchange resins could be used to clean anything contaminated with the amount of petroleum impurities along with the water, as the glycol used in cleaning natural gas. It is not at all clear from these patents how an ionic resin could be integrated into any cleaning apparatus and method used to clean glycols fouled in this manner, it having been thought that the crude oil impurities and the glycol itself would foul the resin such that its use would be foreclosed in any cleaning operation involving glycols.

SUMMARY OF THE INVENTION

The present invention provides a method and associated apparatus by which the complete on-site cleaning of glycols may be effected cheaply and without the need for shutdown. Briefly, the apparatus comprises liquid/gas separating means, hydrocarbon adsorption means, and ion exchange means. Incoming glycol fouled both with hydrocarbons and salts is preliminarily treated to remove both gaseous and liquid hydrocarbons. The glycol so cleaned is then percolated through both anion and cation exchange means such that the exiting glycol contains only water. Throughout the specification allusion to sodium chloride and iron sulphide will be made, and indeed these are the major culprits sought to be removed. However, such allusion is for purposes of example only. Other salts besides these are also present, and the scope of this specification and claims is not intended to be limited to only sodium chloride and iron sulphide.

The removal as ions of salts such as sodium chloride represents a new concept for the removal of salt from glycols in a manner not heretofore seen by the prior art. These ions are removed by strong anion and strong cation exchange resins, and herein lies the secret to processing natural gas in a manner which vastly improves the prior art. Sodium ions are removed by a strong acid cation exchange resin and replaced by hydrogen ions, $H^+$. Chloride ions are removed by a strong base anion exchange resin and replaced by hydroxide ions, $OH^-$. The net effect of the replacement ions $H^+$ and $OH^-$ is to produce water ($H_2O$) which may subsequently be driven off in the plant reboiler after the glycol has been reinjected into the closed loop.

That monoethylene glycol or a polyethylene glycol may be cleaned by passing through an ion exchange resin seems surprising given the organic nature of this material. Ion exchange resins are intended for use in aqueous systems and it was initially thought that the glycol might dissolve or otherwise harm the resin which is itself organic in nature. Given the supposition that some small amount of entrained petroleum hydrocarbon might pass through the resin along with the glycol, it had further been thought that the surface of the resin beads might be blocked, coated, or otherwise "clogged up".

The apparatus (herein also referred to as a glycol cleaning unit, GCU) which performs this entire cleaning operation is compact and may thereby be made mobile by placing it on the bed of a truck or on a trailer such that it may be transported from plant to plant. The turn-around time needed to clean the glycol is short and, accordingly, the method is limited only by the amount of time required to transport a glycol unit to a plant if one is not already present on-site.

Throughout the specification and the claims, the term "glycol" is used generically to refer to a group of liquids having the formula:

$$H\text{-}(O\text{---}CH_2\text{---}CH_2)_n\text{OH}$$

where n may be 1 to 5. The term is not to be regarded as restricting the invention to only one species such as monoethylene glycol, i.e. where $n=1$. Thus, for example, the phrase "a glycol" is generally intended to refer to a compound (or mixture of compounds) selected from the group consisting of monoethylene glycol, diethylene glycol, triethylene glycol, tetraethylene glycol, and pentaethylene glycol, inclusive. Compounds having higher n values higher than 5 may also be present in a mixture as minor constituents, however.

BRIEF DESCRIPTION OF THE DRAWING

These and other objects and advantages of the invention will become more apparent and more readily appreciated from the following detailed description of the presently preferred exemplary embodiment of the invention taken in conjunction with the accompanying drawings, of which:

The single FIGURE schematically shows the apparatus of this invention which is used to clean glycols.

DETAILED DISCUSSION

The FIGURE schematically sets forth in component form one embodiment of the apparatus (GCU) of this invention, and all appertaining component functions may be summarized as follows. Dirty or contaminated glycol, ideally at a temperature of less than 110° F. and an inlet pressure of 80–90 psi is admitted from a processing plant closed loop 11 through inlet 10 and travels through transfer line 12 and flow meter 14 to the liquid/gas separation unit indicated generally at 16, in transit passing pressure gauge 18. The flow of the glycol from the closed loop through the entire GCU can be stepped up at the inlet if desired by means of air driven booster pump 20.

Liquid/gas separation unit 16 includes a receiving tank wherein glycol and other associated liquids collect at the bottom while entrained hydrocarbon and other gaseous contaminants naturally migrate upwards to the dome 22. The immiscible liquid hydrocarbon fraction entrained in the liquid glycol will largely separate therefrom such that two layers are formed. As the hydrocarbon fraction is generally less dense than the glycol, it will separate out as an upper layer sitting atop the lower glycol fraction. At some appropriate or predetermined pressure as indicated by pressure gauge 18, or at regular predetermined intervals, e.g. every couple of minutes, the gaseous constituents in the dome are vented and the liquid hydrocarbon layer is allowed to flow through line 24 to hydrocarbon separator 26. Suitable valve means 28, by which line 24 may be manually opened or closed is situated therein for this purpose. Advantageously, this valve may be left open so that gaseous vapors are continuously vented and no "vapor locks" form in the tank. The gaseous and liquid constituents entering hydrocarbon separator 26 can contain a significant portion of entrained glycol, hydrocarbon separator 26 functioning by allowing the gas and liquid "quiet time" to stand such that any entrained glycol settles out and condenses into a liquid layer beneath the hydrocarbons. The settled glycol may then be pumped back by injection pump 30 through transfer line 32 to the liquid/gas separator 16 and be added to the liquid glycol at the bottom therein. A sight gauge 34 may be provided on the hydrocarbon separator so that the level of glycol may be visually assessed and thereby pumped back when some appropriate amount has accumulated. Accumulated hydrocarbons observable by means of sight gauge 34 on hydrocarbon separator 26 can be removed through dump valve 33 which is connected to hydrocarbon separator 26 through lower sight glass fitting 31. It is necessary only that the glycol level be reduced below the level of lower sight glass fitting 31. During the time which hydrocarbons are being "dumped" from hydrocarbon separator 26, injection pump 30 should be off.

The largely degassed glycol exits the bottom of liquid/gas separator 16 through transfer line 36 to occupy substantially the entire volume of and to percolate through hydrocarbon adsorber unit 38. The hydrocarbon adsorber unit basically comprises a tank which encloses a particulate filter or bed of adsorbent material wherein the particles comprising said bed are approximately 20–40 mesh size, and wherein said bed mechanically filters particulate matter that may be entrained in the glycol down to a level of approximately 35 microns. The adsorbent is additionally capable of adsorbing the bulk of any entrained hydocarbons which were not removed in the liquid/gas separator 16. Advantageously, the bed of adsorbent material is replaced with fresh adsorbent each time a new batch of glycol is to be cleaned. This assures that the maximum amount possible of residual hydrocarbons will be removed before the glycol passes on to the ion resin stages.

The further purified glycol exits at the bottom of hydrocarbon adsorber 38 through transfer line 40 and enters iron separator 42, occupying substantially the entire volume therein. Iron separator 42 is a tank containing a cation exchange resin bed through which the glycol percolates. The cation bed, which can consist of the same resin as that in the sodium separator to be discussed subsequently, is regenerable with a 50–60% by weight sodium chloride solution. Glycol exits at the bottom of this unit and travels via transfer line 44 into substantially the entire volume of sodium separator 46. This unit contains a strong acid cation exchange resin bed which exchanges sodium and other cations in the glycol for hydrogen ions on the resin. The glycol so exchanged leaves the bottom of sodium separator 46 via transfer line 48 and fills substantially the entire volume of chloride separator 50. The chloride separator comprises a tank containing a strong base anion exchange resin bed which exchanges hydroxide ions on the resin for chloride and other anions in the glycol. The hydrogen ions derived from the sodium separator 46 and the hydroxide ions derived from the chloride separator 50 combine to form water, and complete the final process steps of a procedure which yields a glycol substantially cleaned of hydrocarbons and salts. As previously mentioned, the net product of the cleanup operation is water which is subsequently easily removed in the reboiler which is part of the gas processing plant's closed loop system for cleaning freshly drilled natural gas.

Glycol that has no been substantially cleaned of hydrocarbon and salt impurities exits via line 52 to be monitored in a series of quality control steps. Specifically, the glycol may optionally be routed through a pH cell 54 and associated instrumentation 56 to be monitored for its acidic or basic content. That is, if either the acid bed in sodium separator 46 or the base bed in chloride separator 50 has become depleted of exchange capacity, the glycol will experience a sudden raising or lowering of pH corresponding to the ions still being exchanged by the resin bed which has not been so depleted. The glycol may further pass through a conductivity cell 58 which will indicate, even if the pH is substantially neutral, whether all the salt has been removed. Additionally, a pressure gauge 60 may also be included to monitor the pressure driving the glycol and to assure qualitatively that volatile hydrocarbon impurities have in fact been substantially removed.

Assuming that all quality control checks are yielding typical readings, the pH will read approximately 7–8, the pressure, depending on the drop through the system, will read about 40 psi at a temperature of less than about 100° F. and the conductivity will run in the neighborhood of 2–18 megohms. A flow of clean glycol per unit of time may be measured by flow meter 62 and, if necessary, the flow may be suitably increased by means of air driven booster pump 64 which functions to step-up the pressure at the GCU outlet and "ram" the glycol back into gas processing plant closed loop system 11, depending on any back pressure in the loop which must be overcome. If the booster pump is not used, the finished clean glycol can be alternatively routed through bypass transfer line 66, exiting at 68 to enter closed loop system 11 after being monitored for pressure one last time at guage 70.

As previously indicated hydrocarbon vapor migrates upwardly to dome 22 of liquid gas separator 16 and liquid hydrocarbons will form an upper layer over the glycol. The greatest extent of hydrocarbon removal will take place in this separation stage. Nonetheless, it would be unrealistic to expect, and impractical to wait for, complete separation of all hydrocarbons in just this stage. Accordingly, additional gaseous constitutents may continue to separate out in the hydrocarbon adsorber 38, iron separator 42, sodium separator 46, and chloride separator 50, albeit the pressures which develop and the amount of liquid hydrocarbons which separate out will successively diminish as the glycol passes from one stage to the next. Accordingly, each of the tanks is designed to have a dome top wherein (predominantly hydrocarbon) gaseous and liquid constituents may collect. Accordingly each of stages 38, 42, 46 and 50 is provided with transfer lines 72, 74, 76 and 78 respectively through which hydrocarbon vapor or liquid which forms may be vented. Each transfer line may suitably be equipped with valves 80, 82, 84 and 86, respectively so that the hydrocarbon separator may be isolated from the rest of the system independently or, to facilitate backwashing of the system, in unison. Other optional valve means may be inserted where desired throughout the system as shown in the FIGURE. For purposes of this invention, valving the system in such a fashion is well within the capability of one of ordinary skill in the art, and selecting a particular valving configuration represents routine optimization.

Several of the stages contain beds of separation materials (e.g., adsorbent, ion exchange resin) as will subsequently be described, and the glycol which entered at a given pressure level will undergo pressure drops across each of these stages such that the inlet pressure of the glycol will have substantially diminished by the time it leaves chloride separator 50. Advantageously, each stage in addition to liquid/gas separator 16 may be equipped with pressure guages 29, 90, 92, and 94 so that the pressure drop across each stage may be suitably monitored and, in the event the pressure drop across a particular stage becomes inordinately large indicating "clogging", appropriate remedial measures may be taken.

Details of the construction of each stage of the GCU will now be described with particularity, including dimensions, quantities and parameters. It is to be cautioned, however, that the details concerning tank size, amounts of resin, temperature, pressure, etc. is for purposes of example only. Modifications regarding these variables could easily be made by one skilled who wished to tailor or customize the system to his specific needs but, nonetheless, said modifications would fall within the scope of the appended claims.

The construction of the tank used for each of stages 16, 38, 42, 46, and 50 advantageously may be the same. Each tank is constructed to have a top dome welded to the side shell. As shown in FIG. 1, each tank may be similarly domed at the bottom. An entrance port for the glycol is provided just below the top weld seam, which port is provided with transfer piping leading in from the inlet or previous stage. An exit port is suitably placed at the tank bottom and provided with suitable associated transfer piping leading into the next stage. Each tank is additionally provided with a vent port in the top dome and suitable piping and valve means whereby hydrocarbon gas pressure may be relieved and any hydrocarbon liquid may be transferred through said piping into hydrocarbon separator 26.

Each tank except the liquid/gas separator 16 and the hydrocarbon separator 26 is provided in its bottom dome section with three layers of screened, graded gravel which together form a supportive underbedding for the material (adsorbent in hydrocarbon adsorber 38, ion exchange resins in iron separator 42, sodium separator 46, and chloride separator 50) effecting each separation function which underbedding rises to a level just below the exit port (i.e. the bottom weld seam). The bottommost layer comprises gravel having a nominal size of 1 inch, the second or middle layer comprises gravel having a nominal size of ⅜ inch, and the top layer comprises gravel which is only slightly larger than sand and which has a nominal size on the order of ⅛ inch.

A working GCU has in fact been constructed with tanks as described above in part comprising each functional separation unit. Top and bottom domes having diameters between about 24 and about 36 inches were welded to side shells having the same diameter and a side shell height of about five feet. As shown in FIG. 1, each top dome is provided with a manhole and cover as at 21, 23, 25, 27, and 29, the removal of which provides access to the tank interior for admitting fresh carbon or regenerated ion exchange resin. Manholes may also be similarly provided at each tank bottom. The cover is constructed such that it sealingly mates with the manhole so that no pressure leaks develop. Thus the tanks themselves are largely interchangeable and can be used for any of the separation functions depending on what specific separating material is placed therein.

Liquid-gas separating unit 16 essentially amounts to an empty tank wherein glycol is admitted and trickles down the sides. The glycol will settle in the bottom of the tank whereby gas diffuses out and occupies a small headspace thereabove. At some suitable and, perhaps predetermined, pressure the headspace may be relieved by venting the gas through transfer line 24 into hydrocarbon separator 26 such that substantially the entire interior volume of the tank will be fluid occupied. Alternatively, venting may take place continuously as previously described so that no potential for air locks develops at all.

Hydrocarbon adsorber 38 comprises a tank as previously described containing therein a quantity of particulate carbon or other hydrocarbon adsorbent material on an underbedding of gravel. The carbon having a particle size of 20-40 mesh is added in a quantity of about five cubic feet such that a layer about two feet deep is formed. As glycol percolates through the carbon layer, hydrocarbons will be adsorbed onto the surface of the carbon particles and the entire bed will mechanically filter particulate contaminants down to a size of about 35 microns. It is particularly intended that the carbon remove by adsorption the bulk of entrained hydrocarbon contaminants which would otherwise not be removed in liquid/gas separator 16. If finer mechanical separation is desired, a thin (on the order of 1-5 inches) overlayer of diatomaceous earth may be placed atop the carbon resulting in the filtration of particles down to a nominal size of 3 microns.

Iron separator 42 removes mainly iron, calcium, and magnesium ions and comprises a tank as previously described which contains therein a layer of strong acid cation exchange resin. The resin employed may be the same as that used in the sodium separator to be described, except that the resin is used in the sodium ion form rather than the hydrogen ion form. About five cubic feet of resin is used to form a layer approximately two feet thick over the gravel underbedding. The resin is obtainable commercially (see Table 1, infra) generally in the sodium ion form and, therefore, it need not be initially converted. Upon depletion of the resin it may be removed and regenerated with a 50-60% solution of sodium chloride.

Sodium separator 46 which removes sodium and other cations comprises a tank as previously described containing therein a layer of a strong acid cation exchange resin in the acid ($H^+$) form. About five cubic feet of resin in the form of small spherical beads is placed in the tank to be supported by the gravel underbedding. This quantity of resin will form a layer about two feet thick. The resin itself (to be hereinafter described) is generally commercially sold in the sodium ($Na^+$) form and will need to be initially converted into the acid state by percolating a quantity of hydrochloric acid through it. Generally, for this quantity of resin it has been found that a 5-6% solution of hydrochloric acid when percolated through the resin will result in substantially complete conversion.

Chloride separator 50 which removes chloride ions comprises a tank as previously described containing therein a layer of a strong base anion exchange resin in the hydroxide ion ($OH^-$) form. As in the case of the cation separator, about five cubic feet of anion exchange resin in the form of small spherical beads is added atop the gravel underbedding in the chloride separator to form a layer about two feet thick. The resin is generally commercially available in the chloride form and consequently will need to be converted to the hydroxide form by percolating a strong base such as sodium hydroxide. For this quantity of resin it has been found that percolating a 5-6% solution of sodium hydroxide through the resin results in substantially complete conversion. Additionally, chloride separator 50 will remove sulphide ions derived from any iron sulphide which partitioned into the glycol from the natural gas.

As shown in the FIGURE, each separation unit 16, 38, 42, 46 and 50 feeds into hydrocarbon separator unit 26 wherein, on standing, glycol separates out from the vapor and liquid admitted thereto. As previously explained, each of the separation units will contain successively diminishing gaseous and liquid hydrocarbon fractions which in turn will contain some entrained glycol. It is the function of the hydrocarbon separator 26 to permit recovery of as much of this entrained glycol as possible, and it can probably best be thought of as functioning as the converse of liquid/gas separator 16. That is, whereas liquid/gas separator 16 functions by allowing entrained hydrocarbon gas and liquid to separate from a pool of glycol and collect thereabove, hydrocarbon separator 26 functions by allowing entrained glycol to coalesce out of the standing hydrocarbon vapor and liquid and collect therebelow.

In use pH monitoring equipment 54 and 56 will indicate when the cation or anion exchange resin has become depleted of exchange capacity as previously explained. At this point the resin may be removed and regenerated using hydrochloric acid for the cation resin and sodium hydroxide for the anion resin.

The strong base anion and strong acid cation exchange resins used in the present invention are well known to the aqueous ion exchange art and readily commercially obtainable. A typical strong base anion exchange resin used in chloride separator 50 comprises divinylbenzene-crosslinked polystyrene containing quarternary ammonium groups and is typically sold in the chloride form. The resin is formed in small (20-50 mesh) spherical beads. The resin may be converted to the hydroxide form by washing with a 5-10% solution of sodium hydroxide. Upon depletion the resin is simply regenerated in the same fashion by washing the solution of sodium hydroxide through it. An example of a typical commercially obtainable strong base exchange resin is Purolite A-400 (The Purolite Co., Cherry Hill, New Jersey). The strong acid cation exchange resin in sodium separator 46 may typically be a polystyrene resin crosslinked with divinylbenzene and has sulphonic acid functional groups. It too is sold in the form of small spherical beads (wet size 16–40 mesh) usually in the sodium form. An example of a strong acid cation resin which is commercially obtainable is Purolite C-100 (The Purolite Co.).

The above description of specific ion exchange resins is given merely as an example. There are, however, a number of manufacturers that sell both strong acid cation and strong base anion resins which are equivalent for purposes of the present invention. Table 1 is intended to be a non-limiting chart which will enable one skilled in the art to cross-reference from one manufacturer to another and obtain an ion exchange resin usable in the present invention.

TABLE 1

| | CLOSEST COMPETITIVE EQUIVALENTS | | | | |
|---|---|---|---|---|---|
| Purolite | Rohm & Haas | Dow | Ionac | Diamond | |
| *Anion Exchange Resins* | | | | | |
| A-600 | IRA-400 | SBR | ASB-1 | A-109 | |
| A-400 | IRA-402 | SBR-P | ASB-1P | A-101D | |
| A-300 | IRA-410 | SAR | ASB-2 | A-102D/A-104 | |
| A-500 | IRA-900 | MSA-1 | A-641 | A-161 | |
| A-100 | IRA-93/94 | MWA-1 | AFP-329 | A-378 | |
| A-300E | | | A-544 | | |
| *Cation Exchange Resins* | | | | | |
| C-100(Na) | IR-120/130 | HCR-S/HCR-W2 | C-249/C-298 | C-20/C-225 | |
| C-150 | IR-200 | MSC-1 | CFP-110 | C-264 | |
| C-100 × 10 | IR-122/IR-132 | HGR/HGR-W2 | C-250/C-299 | C-20 × 10/C-225 × 10 | |

From the FIGURE it will be apparent to those skilled in the art that the sodium separator and the chloride separator units have each been set up to contain a separate bed of the appropriate resin. It is possible, as well, that both separators 46 and 50 could be combined into a single mixed bed ion exchange separator. However, no advantage is to be gained from this, and it is even possible that the efficiency of ion removal may suffer as a result.

It will be immediately apparent to those skilled in the art that this system possesses terrific advantages beyond those inherent in conventional systems. The entire system may be placed on the bed of a truck and driven from site to site where glycols are cleaned on the spot for immediate reuse in natural gas cleaning operations.

Moreover, although the previously described embodiments have been tailored to the situation wherein the glycol contains significant quantities of entrained hydrocarbon impurities, the present invention may be even more easily adapted to a situation wherein natural gas has been extracted without such impurities, or to a situation wherein the glycol has simply accumulated salts from some other source. The apparatus for cleaning glycols contaminated only with salts (i.e. desalting) and, perhaps, water is simply a cation-separation stage preceeding or followed by an anion separation stage, i.e. the apparatus of the FIGURE without the liquid/gas separator 16, hydrocarbon adsorber 38, and iron separator 42. The glycol, contaminated with a salt such as sodium chloride, is successively percolated through a strong base anion exchange bed and a strong acid cation exchange bed. If the glycol additionally contains impurities such as iron sulphide, iron separator 42 may additionally be included. Advantageously, the quality control equipment of the FIGURE, such as a pH monitor and conductivity monitor, may be included as part of the apparatus for the purposes previously noted. Thus, in the case that the only impurity in a glycol besides water is sodium chloride, iron sulphide, and other ion-exchangeable salts, the present invention offers a fast, economical, and logistically feasible alternative to distillation.

Although only a few exemplary embodiments of this invention have been described in detail above, those skilled in the art will readily appreciate that many modifications are possible in the exemplary embodiment without materially departing from the novel teachings and advantages of this invention. Accordingly, all such modifications are intended to be included within the scope of this invention as defined in the following claims.

What is claimed is:

1. A method of dehydrating natural gas, comprising:
   (a) exposing said natural gas to a glycol of the formula $$H\text{-}(OCH_2\text{-}CH_2)_n\text{-}OH$$

wherein n is 1–5;
   (b) passing said glycol from said step (a) through a first strong acid cation exchange resin in the sodium ion form, a second strong cation exchange resin in the hydrogen ion form, and an anion exchange resin; and
   (c) repeating said step (a) with said glycol obtained from said step (b).

2. The method of claim 1 wherein said anion exchange resin is a strong base anion exchange resin in the hydroxide ion form.

3. A method of dehydrating natural gas, comprising:
   (a) exposing said natural gas to a glycol of the formula $$H\text{-}(OCH_2\text{-}CH_2)_n\text{-}OH$$

wherein n is 1–5;
   (b) separating said glycol obtained from said step (a) from gaseous and immiscible liquid hydrocarbon constituents;
   (c) adsorbing residual hydrocarbons from said glycol from said step (b);
   (d) passing said glycol from said step (c) through a first strong acid cation exchange resin in sodium ion form, a second strong cation exchange resin in the hydrogen ion form, and an anion exchange resin; and
   (e) repeating said step (a) with said glycol obtained from said step (d).

4. The method of claim 3 wherein said residual hydrocarbons are adsorbed onto particulate carbon.

5. The method of claim 3 wherein said anion exchange resin is a strong base anion exchange resin in the hydroxide ion form.

* * * * *